United States Patent [19]

Burns

[11] 4,397,318

[45] Aug. 9, 1983

[54] BLOOD COLLECTOR FOR MICROCOLLECTION CONTAINER

[75] Inventor: James A. Burns, Elizabeth, N.J.

[73] Assignee: Becton Dickinson and Company, Paramus, N.J.

[21] Appl. No.: 291,529

[22] Filed: Aug. 10, 1981

[51] Int. Cl.$^3$ .............................................. A61B 5/14
[52] U.S. Cl. .................................. 128/763; 128/767; 427/2
[58] Field of Search ............................... 128/763–767; 427/2

[56] References Cited

U.S. PATENT DOCUMENTS

| | | | |
|---|---|---|---|
| 3,585,647 | 6/1971 | Gajewski et al. | 427/2 |
| 4,024,857 | 5/1977 | Beecher et al. | 128/763 |
| 4,215,700 | 8/1980 | Crouther et al. | 128/763 |
| 4,250,893 | 2/1981 | White | 128/765 |

Primary Examiner—George F. Lesmes
Assistant Examiner—Nancy A. B. Swisher

[57] ABSTRACT

A cap is provided for a blood microcollection container which cap incorporates a partially open tubular and tapered scoop arrangement for engaging a puncture wound, and rapidly receiving blood from the wound. The scoop arrangement is such that a substantial end surface is provided for engaging a puncture wound for receiving blood, and rapidly transferring it to the microcollection container where a further large abutting angular surface engages the surface of the microcollection container. A vent is incorporated into the cap for air displacement for enhancing the rapid transfer of blood and avoiding coagulation. With this invention, the time of transfer is reduced substantially because a less precise positioning is required of the scoop, and the need to initiate a capillary action is avoided.

16 Claims, 7 Drawing Figures

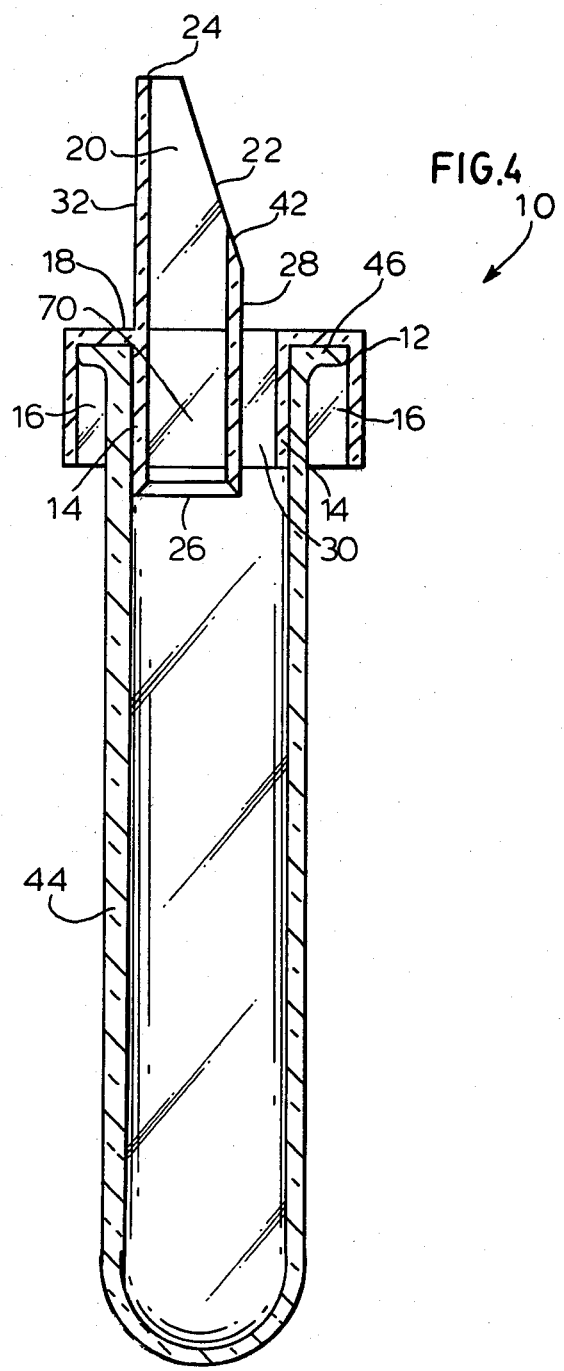

BLOOD COLLECTOR FOR MICROCOLLECTION CONTAINER

BACKGROUND AND STATEMENT OF THE INVENTION

This invention relates to a blood collection device for a microcollection container. More particularly, this invention relates to a scoop type blood collection device wherein a substantially larger engaging surface is provided for engaging the puncture for collecting the blood, and a substantially larger transfer surface is provided for rapidly transferring the blood from the collector into the microcollection container. Because of the relatively large engaging surface for engaging the puncture wound, the arrangement, in accordance herewith, does not require a precise positioning of the scoop engaging surface in order to initiate and rapidly transfer a quantity of blood to the microcollection container.

As will be appreciated by practitioners in the art, recent advancements in analytical instrumentation have made it possible to carry out a variety of hematological diagnostic procedures on very small quantities of blood. Because of this, a patient's finger or earlobe, for example, may be punctured and a very small quantity of blood rapidly collected into a microcollection container for such testing. Such arrangements obviate the need to withdraw venous blood from patients. However, such a collection arrangement must be such that the blood is rapidly collected prior to any coagulation thereof.

In the past, arrangements have been provided wherein a cap or top arrangement is configured to fit on the top of a microcollection container with the top having an integral capillary tube for engaging the puncture and transferring blood to the container. However, with such an arrangement, the tip of the capillary tube must be arraged precisely adjacent the puncture wound and the entire apparatus must be so positioned that the blood flow is along the bottom surface of the tubular microcollection container once the blood passes through the capillary tube in order to engage the surface of the container. Otherwise, if a precise positioning is not carried out, capillary action is not initiated or is slowed, with subsequent clotting. A blood collector of the type utilizing a capillary tube is described in U.S. Pat. No. 4,024,857 issued May 24, 1977.

With this invention, by contrast and as noted above, a scoop arrangement is provided, thus avoiding the need for capillary action. The tip of the scoop has a circumferential or angular extent of about 120° for engaging the puncture wound. Therefore, a much less precise positioning engagement of the wound is required in order to initiate flow of blood rapidly along the scoop of the invention. Furthermore, the angular extent of the inner end of the scoop arrangement is such that a much larger surface is provided for engaging the adjacent surface of the microcollection container at the inner end of the blood flow along the scoop collector of the invention. Thus, even with imprecise positioning, a very rapid transfer of the blood collection takes place.

Other objects and advantages of this invention will be apparent from the following description, the accompanying drawings and the appended claims.

DESCRIPTION OF THE DRAWINGS

FIG. 4 is a side elevational view in section of a microcollection container having disposed on the top thereof an integral scoop collector and top illustrating the invention;

DETAILED DESCRIPTION OF THE INVENTION

Figure 1:
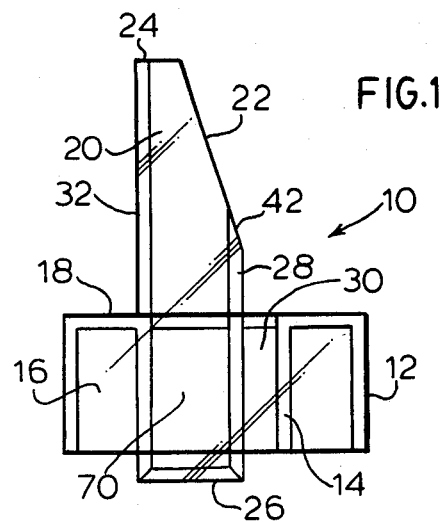
FIG. 1 is a side elevational view of the blood collector of the invention wherein the collector is illustrated as incorporated into a cap or top arrangement for a microcollection container.
Figure 3:
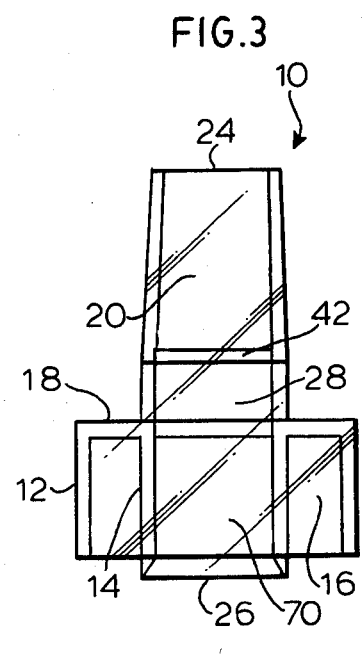
FIG. 3 is a view of the collector of FIG. 1 as viewed from the right-hand side thereof.

Referring to the drawings in which like characters of reference refer to like parts throughout the several views thereof, FIG. 1 illustrates the invention as employed in a cap arrangement wherein the scoop of the invention is integrally formed with the cap.

In FIG. 1, the device 10 includes a cap or top for a microcollection container with concentric spaced apart annular skirts 12, 14 joined together by a top wall 18. The annular space 16 defined by the spaced skirts 12, 14 defines a space for receiving in press fit engagement the top edge of a microcollection tube. This arrangement defines an attaching means. As can be seen in FIG. 1, a tubular microcollection scoop 20 is incorporated into the cap arrangement and extends therethrough from an engaging end 24 to an inner end 26, with the latter for extending into and engaging the adjacent surface of a microcollection container, when the cap or top 10 is positioned on the top edge of the container.

Figure 2:
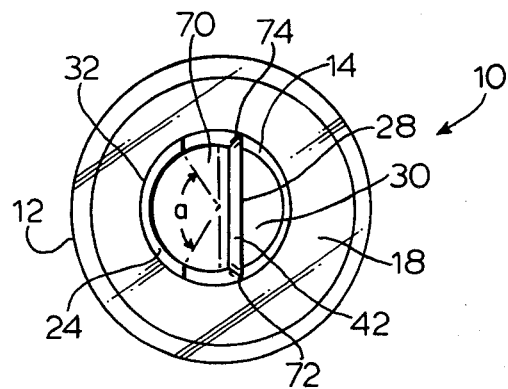
FIG. 2 is a top plan view of the collector of FIG. 1.

The upper portion of scoop 20 does not extend to the outer engaging end 24 of scoop 20, as shown in FIG. 1. The upper wall 28 of scoop 20 ends at 42 to define a tapered upper edge 22 extending from tip 24 to the end 42 of upper wall 28. Upper wall 28 serves as a vane or separator which partially defines a vent area 30 extending through cap 10. The vent provides for air displacement from the microcontainer when blood is introduced into the container through scoop 20. The angular lower wall 32 of scoop 20, at the outer end or tip 24 extends through an angle a, as shown in FIG. 2. That is, viewing the top plan of cap 10 shown in FIG. 2, passage 70 and vent 30 define a circle with an axis. The end edge 24 of scoop 20 extends circumferentially around that circle a 120 degree portion of the 360 degree circle. The end points of that 120 degree portion are marked by angle a. The angle a is about 120° for defining a substantially larger engaging surface for engaging a puncture wound than the angular extent of a capillary tube engaging the same puncture for initiating capillary action.

The upper wall or vein 28 and the lower semicircular wall 32 define the relatively large blood transfer passage 70 for transferring, rapidly, a quantity of blood into the microcollection container. The inner end 26 of the passage 70 has a semi-tubular engaging angular surface defined by the side edges 72, 74 of vein 28, as shown in FIG. 2, with this end surface for engaging the internal surface of the microcollection container being about 220°. The rear end edge 26 of passage 70 extends circumferentially around the circle defined by passage 70 and vent 30, as discussed above, from point 72 to point 74, 220 degrees of the 360 degree circle.

Referring now to FIG. 4, the cap or top 10 of the invention is shown press fit on the upper end 46 of a tubular microcollection container 44. As will be appreciated, other arrangements may be made for engagement and connection of top 10 with the top edge of a microcollection container 44. In addition, the microcollection container may be configured as a cup substantially as described in U.S. Pat. No. 4,024,857, referred to above. As will be appreciated, further, by practitioners in the art, the top may be configured differently as well so long as the scoop arrangement of the invention is configured as shown to extend outwardly and inwardly of the cap with the large engaging tip or outer end 24 for engaging a puncture wound and transferring rapidly blood from the engaging tip to the internal surface of container 44. Moreover, the cap includes a vent 30 for air displacement, as will be appreciated, for the rapid introduction of the collected blood into the container 44. As shown in FIG. 4, vane 28 extends from a point 42 outwardly of the end wall of top surface 18 of cap 10, and inwardly to the inner end 26 of the microcollection scoop arrangement 20 beyond the inner end of vent 30 so as to protect vent 30 from any blockage from overflow or backflow of the collected blood.

Figure 5A:
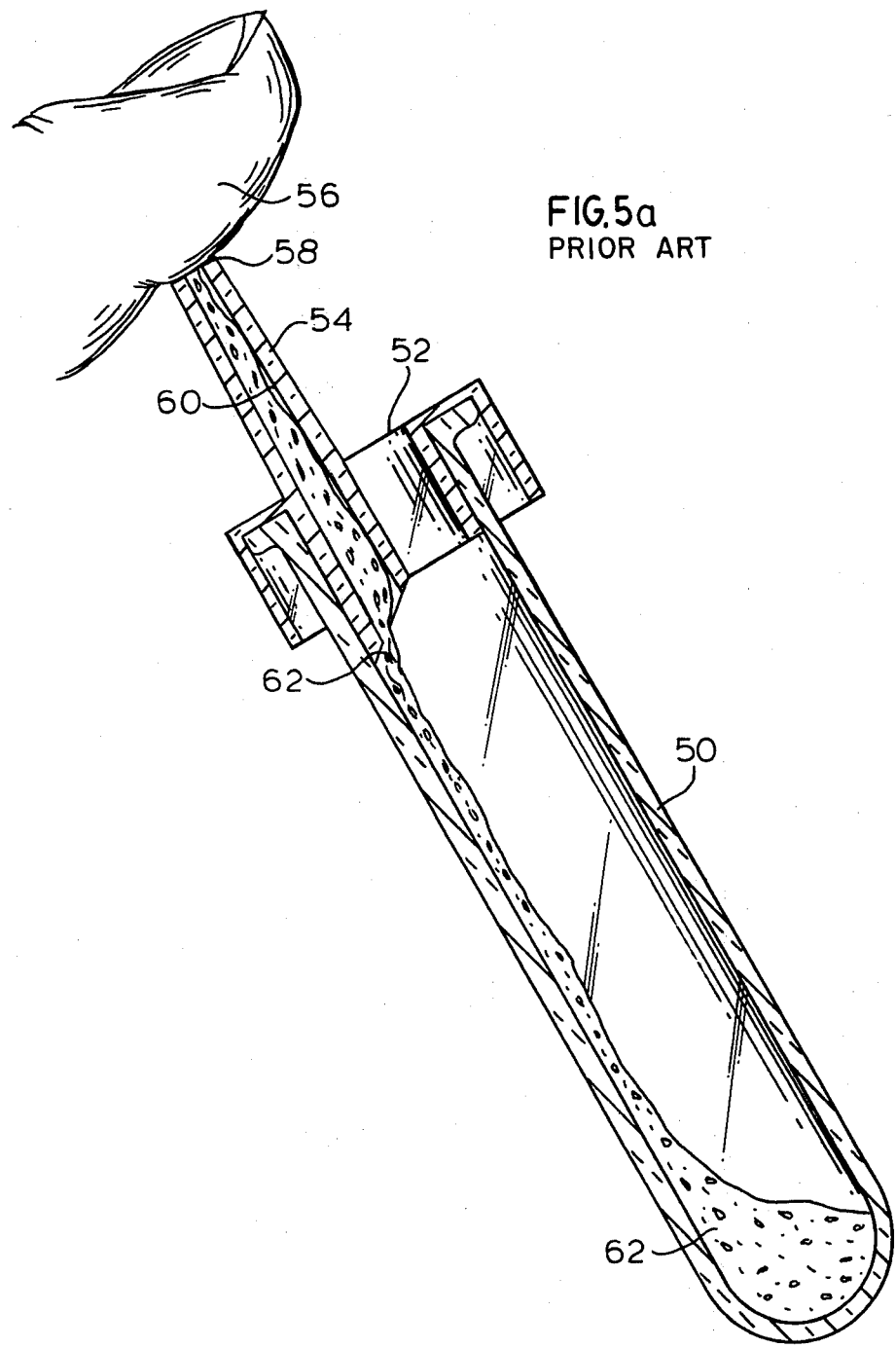
FIG. 5a is a somewhat diagramatic sectional view of a prior art arrangement of blood microcollection device which utilizes a capillary tube.

In FIG. 5, somewhat diagrammatic illustrations of blood collection devices are shown. In FIG. 5a for example, a microcollection container 50 is shown collecting blood from a wound 58 in a finger 56. The blood is being collected through a capillary tube 54 integrally formed in a cap 52 fitted onto container 50. As can be seen in FIG. 5a, the blood 60 reaches a transfer point 62 at the inner end of the capillary tube with the actual point engaging surface of the capillary being over a very small angular extent relative to the internal surface of the microcollection container 50 (that is, the contact area being a point where the two circles coincide).

Figure 5B:
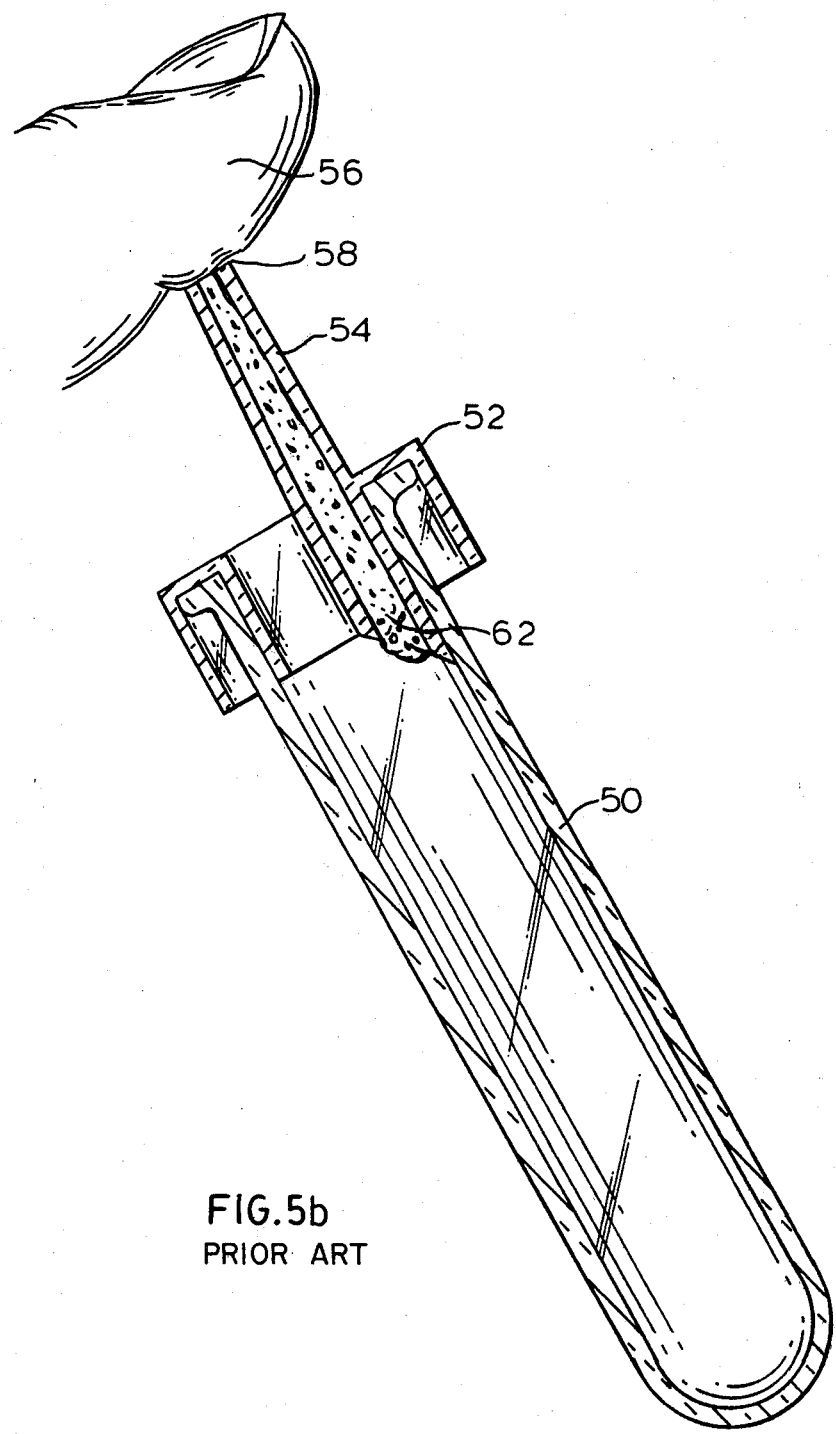
FIG. 5b is a further view of the device in FIG. 5a positioned differently.

FIG. 5a shows the correct positioning of such an arrangement while FIG. 5b shows the incorrect positioning. That is, if a device such as shown and described in FIG. 5a is positioned as shown in FIG. 5b, the capillary action will be slow in taking place because there is little or no surface contact between the inner end of the capillary tube at 62 and the internal surface of the collection container 50. It is important, with such an arrangement, in order to initiate capillary action, to position the arrangement correctly as shown in FIG. 5a.

Figure 5C:
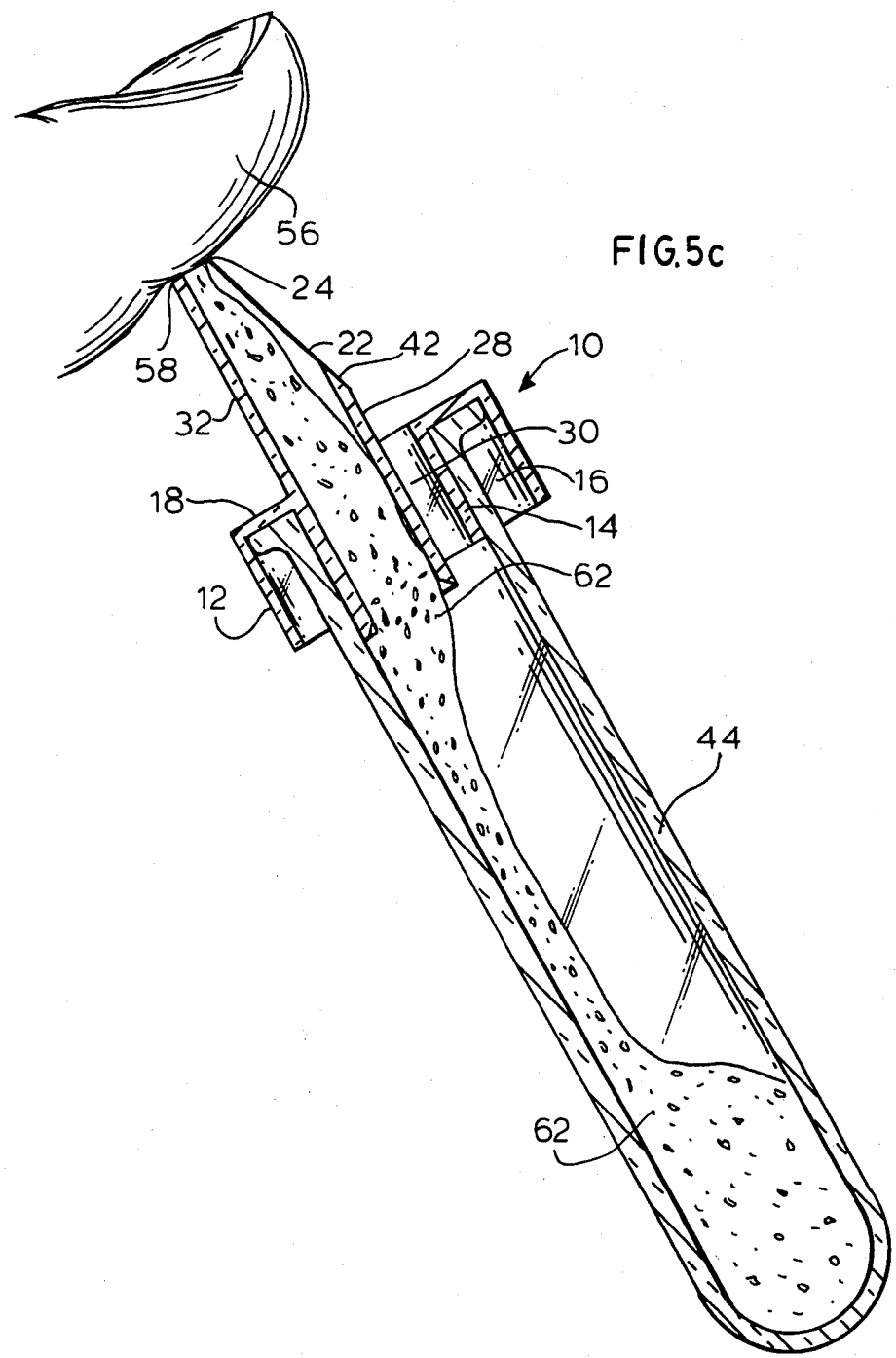
FIG. 5c is a view similar to that of FIGS. 5a and 5b but showing a microcollector device of the invention illustrating the receipt thereof of a quantity of blood from a puncture wound.

By contrast, in FIG. 5c, the arrangement of the invention is shown. The outer engaging tip 24 of the blood collection scoop of the invention, in accordance herewith, has an engaging tip extending over an angular extent of about 120°. Therefore, the relative angular positioning of the collection container 44 need not be nearly so precise in order to provide a proper engagement of the tip 24 for a rapid collection and transfer of blood into the container 44. In addition, the transfer area 62 provides a much larger angular extent, in the neighborhood of 220°, or engaging the internal surface of the microcollection container 44 for preserving the rapid flow of blood into and along the internal surface of container 44. As will be appreciated by practitioners in the art, it is most important for these small quantities of collected blood to be transferred rapidly into the collection container. Otherwise, the blood will clot. This is particularly true with devices utilizing a capillary tube, since the capillary will clot if there is improper bridging between the inner end of the microcollection tube and the inner surface of the collection container.

While the microcollection scoop of the invention may be separately configured to be inserted into a cap for a microcollection container with the scoop incorporating its own defined air vent and protective air vent vane, preferably, the microcollection scoop will be incorporated into an integral structure with the cap or top of the microcollection container involved. Preferably, it will be of a clear molded thermoplastic such as polyethylene, for example. Other materials which may be used, as will be appreciated by practitioners in the art, include various thermoplastics such as polypropylene and polyvinyl chloride. The cap may be comprised of Alathon 20-6064, a polyethylene formulation of DuPont, for example, modified with Atmer 645, a cationic siloxane wetting agent supplied by I.C.I., U.S.A., Wilmington, Delaware. Preferably, the microcollection container will be a clear thermoplastic material such as polypropylene which has been properly treated to provide a hydrophilic internal surface for enhancing the flow of blood introduced into the container. The internal surface of the container may also utilize a surface active agent such as a silicon coating (L520, supplied by Union Carbide).

Whereas, as discussed above, specific embodiments of microcollection containers and associated tops or caps have been shown, it should be understood that it is within the purview of this invention to provide other forms of microcollection containers with differently configured cooperating caps or tops, as long as they can be configured to receive the introduction of the microcollection scoop arrangement of the invention here utilizing an air displacement vent protected by a properly extending separate segregation vane, and so long as the engaging surface at the end 24 of the scoop is configured to provide the large angular extent of engagement for receiving blood from a puncture wound and with the angular extent of the internal surface of the scoop being such as to provide a substantial angular extent for bridging to the internal surface of the associated microcollection container.

While the forms of apparatus herein described constitute preferred embodiments of the invention, it is to be understood that the invention is not limited to these precise forms of apparatus, and that changes may be made therein without departing from the scope of the invention which is defined in the appended claims.

What is claimed is:
1. Blood collection apparatus comprising
    (a) a tube-shaped microcollection container;
    (b) said microcollection container having a closed end and an open end;
    (c) a cap for closing said open end; the improvement characterized by said cap including
        (1) a semi-tubular collector body in said cap having a blood flow passage therethrough;
        (2) said body extending from a puncture wound engaging front end surface to a blood discharge rear end surface;
        (3) means on said cap for attaching said cap to said container open end;
        (4) vent means in said cap for air displacement therethrough;
        (5) a vane in said cap dividing said vent means from said blood flow passage;

(6) said vane defining the upper wall of said passage;

(7) said vane extending from said rear end surface to a point spaced from said front end surface to form semi-tubular scoop means; and (8) said front end surface being the front end of said scoop means and having a large circumferential extent.

2. The apparatus of claim 1, further characterized by
(a) the upper edge of the walls of said semi-tubular body being tapered from said front end surface to the front end edge of said vane.

3. The apparatus of claim 1, further characterized by
(a) said walls of said semi-tubular body extending circumferentially through an angle of about 120° at said front end surface.

4. The apparatus of claim 1, further characterized by
(a) said rear end surface extends rearwardly to a point spaced from said attaching means.

5. The apparatus of claim 1, further characterized by
(a) said rear end surface having a large circumferential extent.

6. The apparatus of claim 5, further characterized by
(a) the walls of said semi-tubular body extending circumferentially through an angle of about 220° at said rear end surface.

7. The apparatus of claim 1, further characterized by
(a) said attaching means comprises
   (1) inner and outer concentric annular skirts spaced from each other to define container end wall engaging surfaces;
   (2) a top wall joining one end of said concentric skirts;
(b) said semi-tubular body extending through said skirts; and
(c) the said front end of said vane extending beyond said top wall.

8. The apparatus of claim 7, further characterized by
(a) said semi-tubular body and said vent means being positioned adjacent to each other in said attaching means separated by said vane;
(b) said adjacent semi-tubular body and said vent means together being annular in cross section; and
(c) a portion of the longitudinal extent of said annular adjacent semi-tubular body and vent means forming said inner skirt.

9. The apparatus of claim 1, further characterized by
(a) said container is comprised of a thermoplastic modified with a cationic siloxane wetting agent.

10. The apparatus of claim 1, further characterized by
(a) said container is comprised of a thermoplastic; and (b) a silicone surface active coating on the internal surfaces of said container for enhancing blood flow thereover.

11. A blood collector closure for a microcollection container; comprising
(a) a cap for engaging the opened end of a microcollection container;
(b) a longitudinally extending semi-tubular body extending through said cap and having a blood flow passage therethrough;
(c) said body extending beyond said cap at each end thereof from a puncture wound engaging front end surface to a blood discharge rear end surface;
(d) vent means in said cap for air displacement therethrough;
(e) a vane on said body defining the upper wall thereof;
(f) said vane extending from said rear end surface to a point spaced from said front end surface to form semi-tubular scoop means; and
(g) said front end surface being the front end of said scoop means and having a large circumferential extent.

12. The apparatus of claim 11, further characterized by
(a) said walls of said semi-tubular body extending circumferentially through an angle of about 120° at said front end surface.

13. The apparatus of claim 11, further characterized by
(a) said rear end surface having a large circumferential extent.

14. The apparatus of claim 13, further characterized by
(a) the walls of said semi-tubular body extending circumferentially through an angle of about 220° at said rear end surface.

15. The apparatus of claim 11, further characterized by
(a) said cap comprises
   (1) inner and outer concentric annular skirts spaced from each other to define a container end wall engaging surface; and
   (2) a top wall joining one end of said concentric skirts 16. The apparatus of claim 15, further characterized by
(a) said semi-tubular body and said vent means being positioned adjacent to each other in said attaching means separated by said vane;
(b) said adjacent semi-tubular body and said vent means together being annular in cross section; and
(c) a portion of the longitudinal extent of said annular adjacent semi-tubular body and vent means forming said inner skirt.

* * * * *